(12) United States Patent
Choi et al.

(10) Patent No.: US 9,456,972 B2
(45) Date of Patent: Oct. 4, 2016

(54) NIACIN-PEPTIDE HAVING SKIN WHITENING ACTIVITY AND USE FOR SAME

(76) Inventors: Sung-Ae Choi, Incheon (KR); Hyuk-Kwang Jeong, Chungcheongnam-do (KR); Young-Mi Byoun, Daejeon (KR); Jun-Seob Shin, Gyeonggi-do (KR); Seo Joon Yoo, Gyeonggi-do (KR); Sang-Chul Yoo, Gyeonggi-do (KR)

( * ) Notice: Subject to any disclaimer, the term of this patent is extended or adjusted under 35 U.S.C. 154(b) by 0 days.

(21) Appl. No.: 14/359,114

(22) PCT Filed: Aug. 22, 2012

(86) PCT No.: PCT/KR2012/006674
§ 371 (c)(1),
(2), (4) Date: May 19, 2014

(87) PCT Pub. No.: WO2013/073763
PCT Pub. Date: May 23, 2013

(65) Prior Publication Data
US 2015/0037268 A1 Feb. 5, 2015

(30) Foreign Application Priority Data
Nov. 18, 2011 (KR) .................. 10-2011-0121135

(51) Int. Cl.
| | | |
|---|---|---|
| *A61K 8/64* | (2006.01) | |
| *A61Q 19/02* | (2006.01) | |
| *C07K 5/00* | (2006.01) | |
| *C07K 7/06* | (2006.01) | |
| *C07K 5/062* | (2006.01) | |
| *C07K 5/083* | (2006.01) | |
| *C07K 5/087* | (2006.01) | |
| *C07K 5/103* | (2006.01) | |
| *C07K 5/11* | (2006.01) | |
| *C07K 5/065* | (2006.01) | |
| *C07K 5/078* | (2006.01) | |
| *C07K 5/072* | (2006.01) | |
| *C07K 5/097* | (2006.01) | |

(52) U.S. Cl.
CPC .............. *A61K 8/64* (2013.01); *A61Q 19/02* (2013.01); *C07K 5/06026* (2013.01); *C07K 5/06052* (2013.01); *C07K 5/06078* (2013.01); *C07K 5/06104* (2013.01); *C07K 5/06156* (2013.01); *C07K 5/06165* (2013.01); *C07K 5/081* (2013.01); *C07K 5/0806* (2013.01); *C07K 5/0812* (2013.01); *C07K 5/0823* (2013.01); *C07K 5/1008* (2013.01); *C07K 5/1013* (2013.01); *C07K 5/1019* (2013.01); *C07K 7/06* (2013.01)

(58) Field of Classification Search
CPC ...... A61K 8/64; A61Q 19/02; C07K 5/0823; C07K 7/06; C07K 5/06026; C07K 5/0806; C07K 5/081; C07K 5/0812; C07K 5/1008; C07K 5/1019; C07K 5/1013; C07K 5/06078; C07K 5/06165; C07K 5/06156; C07K 5/06104; C07K 5/06052
See application file for complete search history.

(56) References Cited

U.S. PATENT DOCUMENTS 4,537,878 A 8/1985 Plotnikoff

FOREIGN PATENT DOCUMENTS

| EP | 2420510 A1 | 2/2012 |
|---|---|---|
| JP | 08-333230 | 12/1996 |
| KR | 10-2008-0047358 | 5/2008 |
| KR | 10-2008-0080907 | 9/2008 |
| KR | 10-0977672 | 8/2010 |
| KR | 10-2010-0097965 | 9/2010 |
| WO | WO 00/62743 | 10/2000 |
| WO | WO 2013/073763 | 5/2013 |

OTHER PUBLICATIONS

Kawashima et al, Antioxidant Properties of Branched-chain Amino Acid Derivatives, Chem. Pharm. Bull., 1979, 27, pp. 1912-1916.*
International Search Report Dated Feb. 28, 2013 From the Korean Intellectual Property Office Re. Application No. PCT/KR2012/006674 and Its Translation Into English.
School of Chemistry and Chemical Enginnering, Henan Univeristry of Technology, Zhengzhou 450001; Henan Institute DF Enginnering, Zhengzhou 451191 (English translation of Abstract), Sep. 24, 2010.
Yao Yong-Feng et al., "Study on the Interaction of Nicotinysalicylic leucyl-histidine and DNA by Ultraviolet Spectroscopy". CCS 15th National Conference of Macrocyclic Chemistry & the 7th National Conference on Supramolecular Chemistry (English translation of Abstract), Oct. 2010.

* cited by examiner

*Primary Examiner* — Julie Ha
*Assistant Examiner* — Li Ni Komatsu
(74) *Attorney, Agent, or Firm* — STIP Law Group, LLC

(57) ABSTRACT

Provided is niacin-peptide which has skin whitening activity. The peptide of the present invention has skin whitening activity by inhibiting melanogenesis, that is, by inhibiting the expression of a gene related to melanogenesis (for example, TRP-1, TRP2, or MIFT). The peptide of the present invention has high stability and skin permeability. Also provided is a cosmetic composition for skin whitening which contains the niacin-peptide.

8 Claims, 9 Drawing Sheets

```
SEQUENCE LISTING

<160> NUMBER OF SEQ ID NOS: 63

<210> SEQ ID NO 1
<211> LENGTH: 2
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 1

Ile Phe
1

<210> SEQ ID NO 2
<211> LENGTH: 2
<212> TYPE: PRT
<213> ORGANISM: Artificial Sequence
<220> FEATURE:
```

```
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 2

Glu Gln
1

<210> SEQ ID NO 3
<211> LENGTH: 2
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 3

Glu Thr
1

<210> SEQ ID NO 4
<211> LENGTH: 2
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: niacin linked to peptide's N-terminal

<400> SEQUENCE: 4

Phe Pro
1

<210> SEQ ID NO 5
<211> LENGTH: 2
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: niacin linked to peptide's N-terminal

<400> SEQUENCE: 5

Asn Ile
1

<210> SEQ ID NO 6
<211> LENGTH: 2
<212> TYPE: PRT
<213> ORGANISM: Artificial Sequence
<220> FEATURE:
<223> OTHER INFORMATION: niacin linked to peptide's N-terminal
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 6

Asn Leu
1
```

```
<210> SEQ ID NO 7
<211> LENGTH: 2
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 7

Asn Pro
1

<210> SEQ ID NO 8
<211> LENGTH: 2
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 8

Asn Tyr
1

<210> SEQ ID NO 9
<211> LENGTH: 2
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 9

Pro Gly
1

<210> SEQ ID NO 10
<211> LENGTH: 2
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 10

Pro Ser
1

<210> SEQ ID NO 11
<211> LENGTH: 2
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide
```

```
<400> SEQUENCE: 11

Gln Ile
1

<210> SEQ ID NO 12
<211> LENGTH: 2
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 12

Val Ala
1

<210> SEQ ID NO 13
<211> LENGTH: 2
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 13

Val Phe
1

<210> SEQ ID NO 14
<211> LENGTH: 2
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 14

Val Ser
1

<210> SEQ ID NO 15
<211> LENGTH: 2
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 15

Val Thr
1

<210> SEQ ID NO 16
<211> LENGTH: 2
<212> TYPE: PRT
<213> ORGANISM: Artificial Sequence
```

```
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 16

Trp Met
1

<210> SEQ ID NO 17
<211> LENGTH: 2
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 17

Tyr Arg
1

<210> SEQ ID NO 18
<211> LENGTH: 2
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 18

Tyr Thr
1

<210> SEQ ID NO 19
<211> LENGTH: 3
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 19

Ala His Lys
1

<210> SEQ ID NO 20
<211> LENGTH: 3
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 20

Phe Trp Tyr
1
```

```
<210> SEQ ID NO 21
<211> LENGTH: 3
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 21

Gly His Arg
1

<210> SEQ ID NO 22
<211> LENGTH: 3
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide
<220> FEATURE:
<221> NAME/KEY: MISC_FEATURE
<222> LOCATION: (3)..(3)
<223> OTHER INFORMATION: Hydroxyproline

<400> SEQUENCE: 22

Gly Pro Xaa
1

<210> SEQ ID NO 23
<211> LENGTH: 3
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 23

Lys Val Lys
1

<210> SEQ ID NO 24
<211> LENGTH: 3
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 24

Thr Tyr Arg
1

<210> SEQ ID NO 25
<211> LENGTH: 3
<212> TYPE: PRT
<213> ORGANISM: Artificial Sequence
<220> FEATURE:
```

```
<223> OTHER INFORMATION: niacin-linked peptide
<220> FEATURE:
<221> NAME/KEY: MISC_FEATURE
<223> OTHER INFORMATION: amidated c terminus
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 25

Tyr Gly Tyr
1

<210> SEQ ID NO 26
<211> LENGTH: 3
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide
<220> FEATURE:
<221> NAME/KEY: MISC_FEATURE
<222> LOCATION: (3)..(3)
<223> OTHER INFORMATION: C' AMIDATED

<400> SEQUENCE: 26

Pro Leu Gly
1

<210> SEQ ID NO 27
<211> LENGTH: 4
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: beta-alanine
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 27

Ala His Ser His
1

<210> SEQ ID NO 28
<211> LENGTH: 4
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 28

Asp Lys Tyr Tyr
1

<210> SEQ ID NO 29
<211> LENGTH: 4
<212> TYPE: PRT
<213> ORGANISM: Artificial Sequence
<220> FEATURE:
```

```
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 29

Gly Glu Pro Gly
1

<210> SEQ ID NO 30
<211> LENGTH: 4
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 30

Gly Gln Pro Arg
1

<210> SEQ ID NO 31
<211> LENGTH: 4
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 31

Gly Arg Lys Gly
1

<210> SEQ ID NO 32
<211> LENGTH: 4
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 32

Lys Ala Lys Ala
1

<210> SEQ ID NO 33
<211> LENGTH: 4
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 33

Ser Ser Asn Ala
1
```

```
<210> SEQ ID NO 34
<211> LENGTH: 4
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 34

Val Pro Ala Ala
1

<210> SEQ ID NO 35
<211> LENGTH: 4
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide
<220> FEATURE:
<221> NAME/KEY: MISC_FEATURE
<222> LOCATION: (4)..(4)
<223> OTHER INFORMATION: C' AMIDATED

<400> SEQUENCE: 35

Tyr Pro Phe Phe
1

<210> SEQ ID NO 36
<211> LENGTH: 5
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide
<220> FEATURE:
<221> NAME/KEY: MISC_FEATURE
<222> LOCATION: (5)..(5)
<223> OTHER INFORMATION: C'  AMIDATED

<400> SEQUENCE: 36

Gly Pro Arg Pro Ala
1               5

<210> SEQ ID NO 37
<211> LENGTH: 6
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 37

Ile Ser Glu Leu Gly Trp
1               5

<210> SEQ ID NO 38
<211> LENGTH: 5
```

```
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 38

Lys Leu Ala Lys Lys
1               5

<210> SEQ ID NO 39
<211> LENGTH: 5
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 39

Lys Arg Gly Asp Arg
1               5

<210> SEQ ID NO 40
<211> LENGTH: 5
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 40

Lys Arg Gly Lys Pro
1               5

<210> SEQ ID NO 41
<211> LENGTH: 5
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 41

Lys Thr Thr Lys Ser
1               5

<210> SEQ ID NO 42
<211> LENGTH: 5
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 42
```

-continued

Lys Val Ala Arg Pro
1               5

<210> SEQ ID NO 43
<211> LENGTH: 5
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 43

Arg Lys Asp Val Tyr
1               5

<210> SEQ ID NO 44
<211> LENGTH: 5
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 44

Tyr Gly Gly Phe Leu
1               5

<210> SEQ ID NO 45
<211> LENGTH: 5
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 45

Tyr Gly Gly Phe Met
1               5

<210> SEQ ID NO 46
<211> LENGTH: 6
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 46

Ser Ile Lys Val Ala Val
1               5

<210> SEQ ID NO 47
<211> LENGTH: 6
<212> TYPE: PRT
<213> ORGANISM: Artificial Sequence
<220> FEATURE:
<223> OTHER INFORMATION: niacin-linked peptide
<220> FEATURE:

```
<221> NAME/KEY: MISC_FEATURE
<222> LOCATION: (1)..(1)
<223> OTHER INFORMATION: N-terminal nicotinoyl conjugated peptide

<400> SEQUENCE: 47

Val Glu Pro Ile Pro Tyr
1               5

<210> SEQ ID NO 48
<211> LENGTH: 6
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 48

Val Gly Val Ala Pro Gly
1               5

<210> SEQ ID NO 49
<211> LENGTH: 6
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide
<220> FEATURE:
<221> NAME/KEY: MISC_FEATURE
<222> LOCATION: (6)..(6)
<223> OTHER INFORMATION: C' AMIDATED

<400> SEQUENCE: 49

Glu Glu Met Gln Arg Arg
1               5

<210> SEQ ID NO 50
<211> LENGTH: 6
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 50

Gly Pro Gln Gly Pro Gln
1               5

<210> SEQ ID NO 51
<211> LENGTH: 6
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 51

Tyr Gly Tyr Thr Gly Ala
```

```
1               5
```

<210> SEQ ID NO 52
<211> LENGTH: 3
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 52

```
Pro Leu Gly
1
```

<210> SEQ ID NO 53
<211> LENGTH: 6
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 53

```
Glu Glu Met Gln Arg Arg
1               5
```

<210> SEQ ID NO 54
<211> LENGTH: 4
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 54

```
Tyr Pro Phe Phe
1
```

<210> SEQ ID NO 55
<211> LENGTH: 5
<212> TYPE: PRT
<213> ORGANISM: Artificial Sequence
<220> FEATURE:
<223> OTHER INFORMATION: niacin-linked peptide
<220> FEATURE:
<221> NAME/KEY: MISC_FEATURE
<222> LOCATION: (1)..(1)
<223> OTHER INFORMATION: N-terminal nicotinoyl conjugated peptide

<400> SEQUENCE: 55

```
Gly Pro Arg Pro Ala
1               5
```

<210> SEQ ID NO 56
<211> LENGTH: 19
<212> TYPE: DNA
<213> ORGANISM: Artificial Sequence
<220> FEATURE:
<223> OTHER INFORMATION: Single strand DNA oligonucleotide

<400> SEQUENCE: 56

-continued

```
tggcccagga tcagtaggt                                              19

<210> SEQ ID NO 57
<211> LENGTH: 17
<212> TYPE: DNA
<213> ORGANISM: Artificial Sequence
<220> FEATURE:
<223> OTHER INFORMATION: Single strand DNA oligonucleotide

<400> SEQUENCE: 57
catcaacact tccagca                                                17

<210> SEQ ID NO 58
<211> LENGTH: 19
<212> TYPE: DNA
<213> ORGANISM: Artificial Sequence
<220> FEATURE:
<223> OTHER INFORMATION: Single strand DNA oligonucleotide

<400> SEQUENCE: 58
ggctacaatt acgccgttg                                              19

<210> SEQ ID NO 59
<211> LENGTH: 22
<212> TYPE: DNA
<213> ORGANISM: Artificial Sequence
<220> FEATURE:
<223> OTHER INFORMATION: Single strand DNA oligonucleotide

<400> SEQUENCE: 59
cactgagaga gttgtggacc aa                                          22

<210> SEQ ID NO 60
<211> LENGTH: 25
<212> TYPE: DNA
<213> ORGANISM: Artificial Sequence
<220> FEATURE:
<223> OTHER INFORMATION: Single strand DNA oligonucleotide

<400> SEQUENCE: 60
cttaactcca actgtgaaaa agagg                                       25

<210> SEQ ID NO 61
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 61
catacctggg actcactctc                                             20

<210> SEQ ID NO 62
<211> LENGTH: 18
<212> TYPE: DNA
<213> ORGANISM: Artificial Sequence
<220> FEATURE:
<223> OTHER INFORMATION: Single strand DNA oligonucleotide

<400> SEQUENCE: 62
gagccaaacg ggtcatca                                               18

<210> SEQ ID NO 63
<211> LENGTH: 19
<212> TYPE: DNA
```

```
<213> ORGANISM: Artificial Sequence
<220> FEATURE:
<223> OTHER INFORMATION: Single strand DNA oligonucleotide

<400> SEQUENCE: 63
catattcgtg gttcacacc                                              19
```

NIACIN-PEPTIDE HAVING SKIN WHITENING ACTIVITY AND USE FOR SAME

CROSS-REFERENCE TO RELATED APPLICATION

This application is a National phase of PCT patent Application No. PCT/KR2012/006674 having International filing date of Aug. 22, 2012 which claims the benefit of priority of Korean Patent Application No. 10-2011-0121135 filed on Nov. 18, 2011. The contents of the above applications are all incorporated by reference as if fully set forth herein in their entirety.

BACKGROUND OF THE INVENTION

1. Field of the Invention

The present invention relates to niacin-peptides having skin whitening effect and uses thereof.

2. Description of the Related Art

The color of human skin varies due to numerous factors involving seasons, human races and sex. The skin color is mainly governed by the amount of melanin, carotene and hemoglobin in which melanin is the most crucial factor. Melanin synthesized in melanocytes in the skin basal layer is transferred to adjacent keratinocytes and then is responsible for the color of human skin. The lack of melanin may induce skin lesions such as leukoplakia whereas an excess production of melanin may generate freckles and blemishes. Melanin is formed by tyrosinase-involving reactions on tyrosine. Since the tyrosinase becomes more active by ultraviolet rays, the skin color becomes darker upon exposure of the skin to sun lights. Cosmetics for skin whitening have established large market in Korea and Japan, most of which contain a mixture of substances having inhibitory effects on the tyrosinase activity.

The reasons why Asians skin is more vulnerable to pigmentation and aging have been completely not suggested yet, while the activities of numerous enzymes implicated in melanogenesis and skin darkness were recently reported. The potential substances capable of brightening dark skin have been usually known to inhibit both melanogenesis and implicated enzymes.

Conventional ingredients as tyrosinase inhibitors introduced into skin whitening cosmetics includes ascorbic acid (Vitamin C) and its derivatives, plant extracts involving Morus Alba Bark extract, green tea extract, aloe extract, Scutellaria Laterifolia extract and so forth, kojic acid, arbutin, oil-soluble glycyrrhiza extract and niacinamide. However, various plant extracts are very likely to show instability and non-lasting effects, when they are introduced into products. Also, their inhibitory effect on the tyrosinase activity is likely to be negligent. Kojic acid conventionally used as tyrosinase inhibitors causes allergic reactions (Nakagawa M. et. al., *Contact Dermatitis*, 43:PP9-3(1995)) and has serious production problems in which it has to be used in relatively excessive amounts (e.g., 2%) due to its instability in products.

Niacinamide approved by KFDA (Korea Food & Drug Administration) as a functional skin whitening material is water-soluble Vitamin B3 also known as nicotinamide. Niacinamide essential for human body is contained in foods such as green vegetables and cereals. The necessity of niacinamide for healthy skin has been recognized since the early $20^{th}$ century. The deficient of Vitamin B3 in diets results in the pellagra causing severe skin lesions; therefore, niacinamide has been also called as Vitamin PP to prevent the disease.

Niacinamide has been reported not to inhibit activity of tyrosinase and dopaoxidase unlike other conventional melanogenesis inhibitors with direct inhibitory effects on melanogenesis, and further not to suppress melanogenesis in cultured melanocytes. Melanosomes carrying melanin generated in melanocytes localized in the basal layer are transferred to keratinocytes through dendrites. Niacinamide has been suggested to only block movement of melanosomes onto the skin surface. It has been well-known for maintenance of bright skin by decreasing melanin movement from melanocytes to keratinocytes by 68%. However, niacinacetate as one of intermediates for niacinamide synthesis remains around 20-100 ppm in the purification process of niacinamide with higher purity. The residual niacinacetate has been reported to show high cytotoxicity.

In spite of numerous attempts to develop skin whitening products using peptides, their skin whitening effects have not been satisfactory yet. Vitamin C-peptide complex and hydro quinone-peptide complex developed to maximize skin whitening effects are problematic in terms of their preparation and cost, resulting in limited application to cosmetic market.

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

For developing novel peptides having skin whitening effects, the present inventors have made intensive researches to screen peptide library linked with niacin. As a result, the present inventors have discovered a novel peptide having superior efficacies as well as improved stability, eventually accomplishing the present invention.

Accordingly, it is one object of this invention to provide niacin-peptides having skin whitening effect.

It is another object of this invention to provide a composition for skin whitening.

It is still another object of this invention to provide a method for skin whitening.

Other objects and advantages of the present invention will become apparent from the following detailed description together with the appended claims and drawings.

In one aspect of this invention, there is provided a peptide having skin whitening effect, characterized in that the peptide is selected from the group consisting of nicotinoyl-IF (SEQ ID NO: 1), nicotinoyl-EQ (SEQ ID NO: 2), nicotinoyl-ET (SEQ ID NO: 3), nicotinoyl-FP (SEQ ID NO: 4), nicotinoyl-NI (SEQ ID NO: 5), nicotinoyl-NL (SEQ ID NO: 6), nicotinoyl-NP (SEQ ID NO: 7), nicotinoyl-NY (SEQ ID NO: 8), nicotinoyl-PG (SEQ ID NO: 9), nicotinoyl-PS (SEQ ID NO: 10), nicotinoyl-QI (SEQ ID NO: 11), nicotinoyl-VA (SEQ ID NO: 12), nicotinoyl-VF (SEQ ID NO: 13), nicotinoyl-VS (SEQ ID NO: 14), nicotinoyl-VT (SEQ ID NO: 15), nicotinoyl-WM (SEQ ID NO: 16), nicotinoyl-YR (SEQ ID NO: 17), nicotinoyl-YT (SEQ ID NO: 18), nicotinoyl-AHK (SEQ ID NO: 19), nicotinoyl-FWY (SEQ ID NO: 20), nicotinoyl-GHR (SEQ ID NO: 21), nicotinoyl-GPHyp (SEQ ID NO: 22), nicotinoyl-KVK (SEQ ID NO: 23), nicotinoyl-TYR (SEQ ID NO: 24), nicotinoyl-YGY (SEQ ID NO: 25), nicotinoyl-PLG-NH2 (SEQ ID NO: 26), nicotinoyl-beta-AHSH (SEQ ID NO: 27), nicotinoyl-DKYV (SEQ ID NO: 28), nicotinoyl-GEPG (SEQ ID NO: 29), nicotinoyl-GQPR (SEQ ID NO: 30), nicotinoyl-GRKG (SEQ ID NO: 31), nicotinoyl-KAKA (SEQ ID NO: 32), nicotinoyl-SSNA (SEQ ID NO: 33), nicotinoyl-VPAA (SEQ ID NO: 34), nicotinoyl-YPFF-NH2 (SEQ ID NO: 35), nicotinoyl-GPRPA-NH2 (SEQ ID NO: 36), nicotinoyl-ISELGW (SEQ ID NO: 37), nicotinoyl-KLAKK (SEQ ID NO: 38), nicotinoyl-KRGDR (SEQ ID NO: 39), nicotinoyl-KRGKP (SEQ ID NO: 40), nicotinoyl-KTTKS (SEQ ID NO: 41), nicotinoyl-KVARP (SEQ ID NO: 42), nicotinoyl-RKDVY (SEQ ID NO: 43), nicotinoyl-YGGFL (SEQ ID NO: 44), nicotinoyl-YGGFM (SEQ ID NO: 45), nicotinoyl-SIKVAV (SEQ ID NO: 46), nicotinoyl-VEPIPY (SEQ ID NO: 47), nicotinoyl-VGYAPG (SEQ ID NO: 48), nicotinoyl-EEMQRR-NH2 (SEQ ID NO: 49), nicotinoyl-GPQGPQ (SEQ ID NO: 50), nicotinoyl-YGYTGA (SEQ ID NO: 51). For developing novel peptides having skin whitening effects, the present inventors have made intensive researches to screen peptides from niacin-linked peptide libraries, finally discovering some peptides linked with niacin showing skin whitening effect by inhibiting melanogenesis.

The present inventors have constructed various peptide libraries having a niacin group linked to their N-terminal to prepare candidate peptides, and then screened peptides having superior activity in inhibition of melanogenesis.

The term used herein "peptide" refers to a linear molecule formed by linking amino acid residues through peptide bonds. The niacin-peptide refers to a peptide derivative formed by linking niacin to the N-terminal of a peptide.

The peptides of the invention may be prepared by conventional chemical synthesis processes known to one of skill in the art, in particular, solid-phase synthesis techniques (Merrifield, J. Amer. Chem. Soc., 85: 2149-54 (1963); Stewart, et al, *Solid Phase Peptide Synthesis*, 2nd. ed., Pierce Chem. Co.: Rockford, 111 (1984)).

According to a preferable embodiment, the peptide of the present invention may be modified by linking niacin to their N-terminal. The peptide of the present invention may possess enhanced in vivo stability to show prolonged half-life.

According to a preferable embodiment, the peptide of the present invention may be modified by linking a $NH_2$ group to its C-terminal.

The modifications of peptides described above greatly increase the stability of the peptides of this invention. The term used herein "stability" refers to in vivo stability and storage stability (e.g., storage stability at room temperature) as well. The protection group described above protects the peptides from the attack of protease in vivo.

According to a preferable embodiment, the peptide of the present invention has no toxicity to human cells and therefore has higher applicability to skin whitening. According to the present invention, when HaCat cells and NIH3T3 cells were treated with niacin-peptides in dosages of 10 ng/ml-100 μg/ml, noticeable cytotoxicity was not measured. Also, visible changes in cellular morphology were not observed (FIG. 9). According to the present invention, niacin-peptides exhibit excellent heat stability even at 40° C. (FIG. 3) and have longer action period than niacin-unlinked peptides owing to higher serum stability (FIG. 4). Therefore, the peptides of the present invention may be greatly advantageous in application to products such as pharmaceutical compositions, quasi-drugs and cosmetics requiring long-term storage.

According to a preferable embodiment, the peptides of the present invention have an ability to inhibit melanogenesis. According to the present invention, when melanocytes were treated with α-MSH to induce melanogenesis and then with the present peptide, followed by measuring the amount of melanin generated. The melanogenesis in niacin-peptide treated groups was inhibited by about 4-44% compared with that in the control group (Table 1). Specially, the inhibition rates of melanogenesis by treating nicotinoyl-ET, nicotinoyl-PG, nicotinoyl-PS and nicotinoyl-VS were 40%, 30%, 44% and 35%, respectively.

According to a preferable embodiment, the peptide of the present invention inhibits melanogenesis in a dose-dependent manner. According to the present invention, cells were incubated with NA-PS and niacin-unlinked peptides (1 μg/ml, 10 μg/ml, 100 μg/nil and 250 μg/ml) for 3 days and the extent of melanogenesis was observed. The color of medium became transparent by incubation of niacin-peptides in a concentration-dependent manner (FIG. 5). Cells in medium were incubated with various concentrations of niacin-peptides, niacin-unlinked peptides, arbutin and AA2G (1 μg/ml, 10 μg/ml, 100 μg/ml, 250 μg/ml) for 3 days, the absorbances of the medium at 490 nm were measured. It was verified that the amount of melanogenesis by niacin-peptide was significantly decreased compared with the niacin-unlinked peptide (FIG. 6).

According to a preferable embodiment, the peptide of the present invention inhibits the activity of tyrosinase. L-tyrosine or peptides (nicotinoyl-PS or PS) were incubated with tyrosinase and the absorbances of the reaction resultant at 475 nm were measured. The tyrosinase activity in the niacin-peptide treated group (nicotinoyl-PS) was significantly inhibited compared with that in the niacin-unlinked peptide treated group and arbutin treated group (FIG. 7).

According to a preferable embodiment, the present peptide of the invention suppresses the expression of tyrosinase-related protein-1 (Trp-1), tyrosinase-related protein-2 (Trp-2) and microphtnalmia-associated transcription factor (MITF) gene. Melanin is generated by a series of enzymatic reactions involving tyrosinase, TRP-1, TRP-2, and so forth (Olivares et al., *Pigment Cell Melanoma Res* 22(6): 750-760(2009)). Melanogeneis is mainly governed by the proliferation of melanocytes and the increase in the tyrosinase activity. Tyrosinase as a rate limiting factor for melanin biosynthesis at an early stage plays the most crucial role in melanogeneis, converting tyrosine to 3,4-dihydroxy-phenyl-alanine (DOPA) and DOPA quinine to produce reddish eumelanin and brownish pheomelanin (Lopezet et al., *J Biol Chem* 267: 381-390(1992)). TRP-1 and TRP-2 are important enzymes to generate eumelanin. microphtnalmia-associated transcription factor (MITF) is responsible for the transcription of tyrosinase and TRPs. The inhibition of the expression of MITF, TRP-1 and TRP-2 may suppress melanogenesis.

According to the present invention, melanocytes were incubated with α-MSH and peptides (PG, PS, ET, VS) or α-MSH and niacin-peptides (nicotinoyl-PG, nicotinoyl-PS, nicotinoyl-ET, nicotinoyl-VS) (1 μg/ml, 10 μg/ml and 50 μg/ml) for 4 days, and subjected to RT-PCR analysis using mRNA obtained from melanocytes. It was verified that the expression of the genes (TRP-1, TRP-2, MITF) associated with melanogenesis was suppressed in niacin-peptide treated groups (FIG. 8c). These results suggest that the present peptide of the invention has outstanding effect on skin whitening by inhibiting the expression of genes associated with melanogenesis. A cosmetic composition comprising the peptide of the present invention may be provided in various forms to be effectively used for skin whitening.

In another aspect of this invention, there is provided a composition for skin whitening, comprising a peptide selected from the group consisting of nicotinoyl-IF (SEQ ID NO: 1), nicotinoyl-EQ (SEQ ID NO: 2), nicotinoyl-ET (SEQ ID NO: 3), nicotinoyl-FP (SEQ ID NO: 4), nicotinoyl-NI (SEQ ID NO: 5), nicotinoyl-NL (SEQ ID NO: 6), nicotinoyl-NP (SEQ ID NO: 7), nicotinoyl-NY (SEQ ID NO: 8), nicotinoyl-PG (SEQ ID NO: 9), nicotinoyl-PS (SEQ ID NO: 10), nicotinoyl-QI (SEQ ID NO: 11), nicotinoyl-VA (SEQ ID NO: 12), nicotinoyl-VF (SEQ ID NO: 13), nicotinoyl-VS (SEQ ID NO: 14), nicotinoyl-VT (SEQ ID NO: 15), nicotinoyl-WM (SEQ ID NO: 16), nicotinoyl-YR (SEQ ID NO: 17), nicotinoyl-YT (SEQ ID NO: 18), nicotinoyl-AHK (SEQ ID NO: 19), nicotinoyl-FWY (SEQ ID NO: 20), nicotinoyl-GHR (SEQ ID NO: 21), nicotinoyl-GPHyp (SEQ ID NO: 22), nicotinoyl-KVK (SEQ ID NO: 23), nicotinoyl-TYR (SEQ ID NO: 24), nicotinoyl-YGY (SEQ ID NO: 25), nicotinoyl-PLG-NH2 (SEQ ID NO: 26), nicotinoyl-beta-AHSH (SEQ ID NO: 27), nicotinoyl-DKYV (SEQ ID NO: 28), nicotinoyl-GEPG (SEQ ID NO: 29), nicotinoyl-GQPR (SEQ ID NO: 30), nicotinoyl-GRKG (SEQ ID NO: 31), nicotinoyl-KAKA (SEQ ID NO: 32), nicotinoyl-SSNA (SEQ ID NO: 33), nicotinoyl-VPAA (SEQ ID NO: 34), nicotinoyl-YPFF-NH2 (SEQ ID NO: 35), nicotinoyl-GPRPA-NH2 (SEQ ID NO: 36), nicotinoyl-ISELGW (SEQ ID NO: 37), nicotinoyl-KLAKK (SEQ ID NO: 38), nicotinoyl-KRGDR (SEQ ID NO: 39), nicotinoyl-KRGKP (SEQ ID NO: 40), nicotinoyl-KTTKS (SEQ ID NO: 41), nicotinoyl-KVARP (SEQ ID NO: 42), nicotinoyl-RKDVY (SEQ ID NO: 43), nicotinoyl-YGGFL (SEQ ID NO: 44), nicotinoyl-YGGFM (SEQ ID NO: 45), nicotinoyl-SIKVAV (SEQ ID NO: 46), nicotinoyl-VEPIPY (SEQ ID NO: 47), nicotinoyl-VGYAPG (SEQ ID NO: 48), nicotinoyl-EEMQRR-NH2 (SEQ ID NO: 49), nicotinoyl-GPQGPQ (SEQ ID NO: 50), nicotinoyl-YGYTGA (SEQ ID NO: 51).

The present composition may be prepared as a cosmetic composition.

In the present composition, niacin-peptides consisting of 2-6 amino acid residues and serving as an active ingredient have excellent skin permeability due to their small molecular weights. Therefore, the present composition may accomplish skin whitening effects due to its higher skin permeability when it is locally administrated onto skin. The composition of the present invention brightens skin color and preserves skin tone by inhibition of melanogenesis, and is effective on removal of skin pigments and age spots. The niacin-peptide of the present invention inhibits melanogenesis in keratinocytes in several processes, and prevents release of melanin generated to brighten the color of keratinocyte layers.

The cosmetic composition of the present invention may comprise, in addition to nicotinoyl-peptide as the active ingredient, ingredients commonly added for preparation of cosmetic composition. For example, stabilizers, solubilizers, vitamins, colorants, odor improvers or mixtures of these substances may be added.

The cosmetic compositions of this invention may be formulated in a wide variety of forms, for example, including a solution, a suspension, an emulsion, a paste, an ointment, a gel, a cream, a lotion, a powder, soap, a surfactant-containing cleanser, an oil, a powder foundation, an emulsion foundation, a wax foundation and a spray. Specifically, the cosmetic compositions of this invention may be formulated in the form of skin softener, nutrient liquid, nutrient cream, massage cream, essence, eye cream, cleansing cream, cleansing foam, cleansing water, pack, spray or powder.

Where the cosmetic composition is in the form of paste, cream or gel, it may comprise animal and vegetable fats, waxes, paraffins, starch, tragacanth, cellulose derivatives, polyethylene glycols, silicones, bentonites, silica, talc or zinc oxide.

In the formulation of powder or spray, it may comprise lactose, talc, silica, aluminum hydroxide, calcium silicate or polyamide powder. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may comprise liquid diluents, for example water, ethanol or propylene glycol, suspending agents such as ethoxylated isostearyl alcohols, polyoxyethylene sorbitol esters and poly oxyethylene sorbitan esters, microcrystalline cellulose, aluminum metahydroxide, bentonite, agar or tragacanth.

The formulation of cleansing compositions with surfactant may comprise aliphatic alcohol sulfate, aliphatic alcohol ether sulfate, sulfosuccinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives or ethoxylated glycerol fatty acid ester.

In still another aspect of this invention there is provided a method for skin whitening, comprising administering to a subject in need thereof a composition comprising as an active ingredient a peptide selected from the group consisting of nicotinoyl-IF (SEQ ID NO: 1), nicotinoyl-EQ (SEQ ID NO: 2), nicotinoyl-ET (SEQ ID NO: 3), nicotinoyl-FP (SEQ ID NO: 4), nicotinoyl-NI (SEQ ID NO: 5), nicotinoyl-NL (SEQ ID NO: 6), nicotinoyl-NP (SEQ ID NO: 7), nicotinoyl-NY (SEQ ID NO: 8), nicotinoyl-PG (SEQ ID NO: 9), nicotinoyl-PS (SEQ ID NO: 10), nicotinoyl-QI (SEQ ID NO: 11), nicotinoyl-VA (SEQ ID NO: 12), nicotinoyl-VF (SEQ ID NO: 13), nicotinoyl-VS (SEQ ID NO: 14), nicotinoyl-VT (SEQ ID NO: 15), nicotinoyl-WM (SEQ ID NO: 16), nicotinoyl-YR (SEQ ID NO: 17), nicotinoyl-YT (SEQ ID NO: 18), nicotinoyl-AHK (SEQ ID NO: 19), nicotinoyl-FWY (SEQ ID NO: 20), nicotinoyl-GHR (SEQ ID NO: 21), nicotinoyl-GPHyp (SEQ ID NO: 22), nicotinoyl-KVK (SEQ ID NO: 23), nicotinoyl-TYR (SEQ ID NO: 24), nicotinoyl-YGY (SEQ ID NO: 25), nicotinoyl-PLG-NH2 (SEQ ID NO: 26), nicotinoyl-beta-AHSH (SEQ ID NO: 27), nicotinoyl-DKYV (SEQ ID NO: 28), nicotinoyl-GEPG (SEQ ID NO: 29), nicotinoyl-GQPR (SEQ ID NO: 30), nicotinoyl-GRKG (SEQ ID NO: 31), nicotinoyl-KAKA (SEQ ID NO: 32), nicotinoyl-SSNA (SEQ ID NO: 33), nicotinoyl-VPAA (SEQ ID NO: 34), nicotinoyl-YPFF-NH2 (SEQ ID NO: 35), nicotinoyl-GPRPA-NH2 (SEQ ID NO: 36), nicotinoyl-ISELGW (SEQ ID NO: 37), nicotinoyl-KLAKK (SEQ ID NO: 38), nicotinoyl-KRGDR (SEQ ID NO: 39), nicotinoyl-KRGKP (SEQ ID NO: 40), nicotinoyl-KTTKS (SEQ ID NO: 41), nicotinoyl-KVARP (SEQ ID NO: 42), nicotinoyl-RKDVY (SEQ ID NO: 43), nicotinoyl-YGGFL (SEQ ID NO: 44), nicotinoyl-YGGFM (SEQ ID NO: 45), nicotinoyl-SIKVAV (SEQ ID NO: 46), nicotinoyl-VEPIPY (SEQ ID NO: 47), nicotinoyl-VGYAPG (SEQ ID NO: 48), nicotinoyl-EEMQRR-NH2 (SEQ ID NO: 49), nicotinoyl-GPQGPQ (SEQ ID NO: 50), nicotinoyl-YGYTGA (SEQ ID NO: 51).

The features and advantages of the present invention will be summarized as follows:

(a) The niacin-peptide of the present invention possesses outstanding effects on skin whitening by inhibition of melanogenesis;

(b) the peptide of the present invention has excellent stability and skin permeability;

(c) the cosmetic composition containing the present peptide shows excellent effect on skin whitening; and (d) the outstanding activity and stability of the present peptide described above may be greatly advantageous in application to cosmetics for skin whitening.

Figure 1:
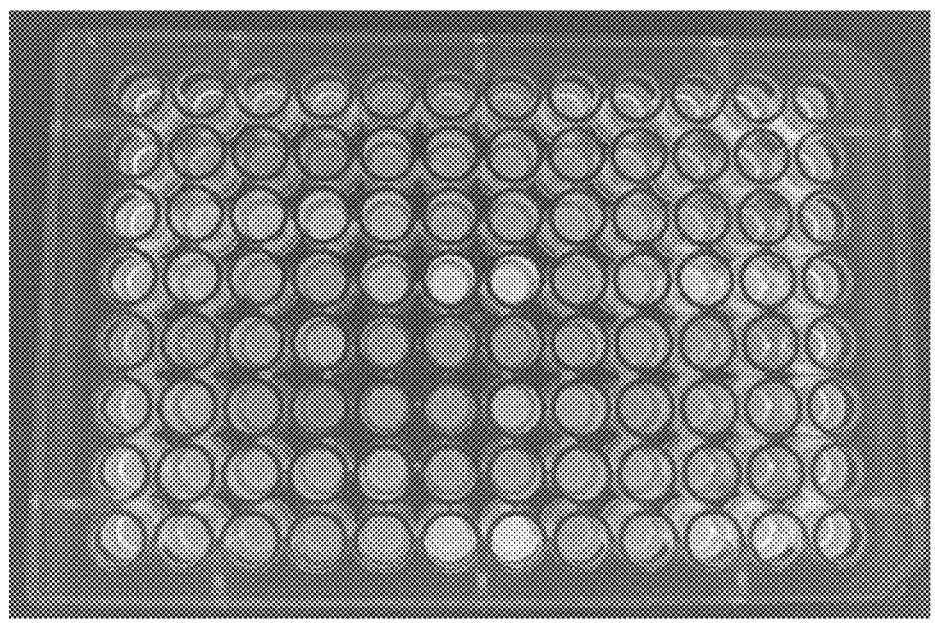
FIG. 1 is the screening results from niacin-peptide libraries for skin whitening.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Synthesis of Peptide Library

To synthesize niacin-peptide library, 50 mg of chloro trityl chloride resin (CTL resin, Nova Biochem Cat No. 01-64-0021) with 19 Fmoc-amino acid (Fmoc-Ala, Fmoc-Arg (pbf), Fmoc-Asp(OtBu), Fmoc-Asn(trt), Fmoc-Gly, Fmoc-Glu(OtBu), Fmoc-Gln(trt), Fmoc-His(trt), Fmoc Ser(tBu), Fmoc-Thr(tBu), Fmoc-Tyr(tBu), Fmoc-Trp(Boc), Fmoc-Leu, Fmoc-Ile, Fmoc-Val, Fmoc-Phe, Fmoc-Met, Fmoc-Lys (Boc), Fmoc-Pro, respectively) were introduced into a 96-well teflon reactor for each series, to which 1 ml of methylene chloride (MC) were added, followed by agitation for 3 min. After removing solution, 1 ml of dimethylformamide (DMF) were added to the resultant and then agitation was carried out for 3 min, after which the solvent was removed. 1 ml of 20% piperidine/DMF were added to the reactor and then agitation was carried out for 10 min at room temperature, after which the solvent was removed. After adding the same volume of the deprotection solution (20% piperidine/DMF), the reaction was undertaken for 10 min and solution was removed, followed by washing sequentially with DMF (2 times), MC (1 time) and DMF (1 time) (each for 3 min) to remove Fmoc-protecting group.

1 ml of methylene chloride solution were introduced into each 96-well reactor, to which 20 μmole of 19 N-α-Niacin-Amino-Acid (or Fmoc-Amino-Acid coincident with sequence) for each series, 40 μmole of DIPEA (diisopropyl ethylamine), 20 μmole of HOBt (N-Hydroxybenzotriazole) and 20 μmole of BOP (Benzotriazole-1-yloxy-tris(dimethyl amino)-phosphonium hexafluorophosphate) were added, followed by agitation for 1 hr. Following the removal of the reaction solution, the resultant was agitated three times (each for 5 min) with DMF solution to remove unreacted residuals. A small amount of the reacted resin was taken to evaluate extent of reactions by Ninhydrine test. In some cases, deprotection and peptide synthesis were repeated according to the planned peptide sequence of 3-6 mer. The prepared niacin-peptidyl resins were washed three times with DMF, MC and methanol, respectively, and gradually dried under nitrogen atmosphere, after which it was completely vacuum-dried under $P_2O_5$. The dried resins were reacted with 30 ml of a leaving solution [containing 81.5% trifluroacetic acid (TFA), 5% distilled water, 5% thioanisole, 5% phenol, 2.5% 1,2-Ethanedithiol (EDT) and 1% Triisopropylsilane (TIS)] for 1 hr in ice water tank upon intermittent agitating. The resin was filtered and washed with a small volume of TFA solution, after which the filtrate was combined with the mother liquor. After distillation under reduced pressure to reduce the total volume by two, the precipitation was induced using 5 ml of cold ether and the formed precipitates were collected by centrifugation, followed by washing twice with cold ether. After removing the mother liquor, the resultant was completely dried under nitrogen atmosphere to yield unpurified niacin-peptides.

Example 2

Screening of Niacin-Peptides

The present inventors screened skin whitening peptides by measuring decrease in melanogenesis using the niacin-peptide libraries prepared in Example 1. B16F10 melanocytes (the Korean Cell Line Bank) were incubated with α-MSH to induce melanogenesis and the inhibition of melanogenesis by the peptide libraries was analyzed. The mouse melanocytes were cultured at 37° C. in 5% $CO_2$ atmosphere in DMEM supplemented with 10% FBS. The cells were seeded in each well of a 96-well plate ($5 \times 10^4$ cells/well) and their attachment was verified. Afterwards, the control group was incubated with only solvent, the positive control group was incubated with 20 μg/ml of α-MSH and the other wells was incubated with 20 μg/ml of α-MSH and 10 ng/ml of peptides for 3 days. After centrifugation, the culture medium was removed and the levels of melanogenesis were observed with a naked eye.

The inhibition rates of melanogenesis by treatment of each peptide prepared in Example 1 were measured at UV 490 nm. The inhibition rates were calculated using the absorbance value of the positive control group incubated with only α-MSH as a standard, which are summarized in Table 1. The candidate peptides analyzed to show excellent screening results were selected and synthesized in a 100-μmole scale for further experiments. FIG. 1 represents the screening result of niacin-peptides.

TABLE 1

Screening value of each synthesized peptide: Inhibition of melanogenesis against α-MSH

| No. | Name | Screening value |
|-----|------|-----------------|
| 1 | nicotinoyl-IF | 1 |
| 2 | nicotinoyl-EQ | 0.9 |
| 3 | nicotinoyl-ET | 0.60 |
| 4 | nicotinoyl-FP | 0.8 |
| 5 | nicotinoyl-NI | 0.8 |
| 6 | nicotinoyl-NL | 0.8 |
| 7 | nicotinoyl-NP | 0.8 |
| 8 | nicotinoyl-NY | 0.8 |
| 9 | nicotinoyl-PG | 0.70 |
| 10 | nicotinoyl-PS | 0.56 |
| 11 | nicotinoyl-QI | 0.82 |
| 12 | nicotinoyl-VA | 0.83 |
| 13 | nicotinoyl-VF | 0.81 |
| 14 | nicotinoyl-VS | 0.65 |
| 15 | nicotinoyl-VT | 0.78 |
| 16 | nicotinoyl-WM | 0.81 |
| 17 | nicotinoyl-YR | 0.79 |
| 18 | nicotinoyl-YT | 0.75 |
| 19 | nicotinoyl-AHK | 0.8 |
| 20 | nicotinoyl-FWY | 0.61 |
| 21 | nicotinoyl-GHR | 0.75 |
| 22 | nicotinoyl-GPHyp | 0.89 |
| 23 | nicotinoyl-KVK | 1.01 |
| 24 | nicotinoyl-TYR | 0.72 |
| 25 | nicotinoyl-YGY | 0.69 |
| 26 | nicotinoyl-PLG-NH2 | 0.92 |
| 27 | nicotinoyl-beta-AHSH | 0.82 |
| 28 | nicotinoyl-DKYV | 0.87 |
| 29 | nicotinoyl-GEPG | 0.96 |
| 30 | nicotinoyl-GQPR | 0.83 |
| 31 | nicotinoyl-GRKG | 0.93 |
| 32 | nicotinoyl-KAKA | 0.87 |
| 33 | nicotinoyl-SSNA | 0.71 |
| 34 | nicotinoyl-VPAA | 0.85 |
| 35 | nicotinoyl-YPFF-NH2 | 0.85 |
| 36 | nicotinoyl-GPRPA-NH2 | 0.7 |
| 37 | nicotinoyl-ISELGW | 0.64 |
| 38 | nicotinoyl-KLAKK | 0.96 |
| 39 | nicotinoyl-KRGDR | 0.92 |
| 40 | nicotinoyl-KRGKP | 0.84 |
| 41 | nicotinoyl-KTTKS | 0.92 |
| 42 | nicotinoyl-KVARP | 0.96 |
| 43 | nicotinoyl-RKDVY | 0.87 |
| 44 | nicotinoyl-YGGFL | 0.78 |
| 45 | nicotinoyl-YGGFM | 0.81 |
| 46 | nicotinoyl-SIKVAV | 0.72 |
| 47 | nicotinoyl-VEPIPY | 0.81 |
| 48 | nicotinoyl-VGVAPG | 0.95 |
| 49 | nicotinoyl-EEMQRR-NH2 | 0.86 |
| 50 | nicotinoyl-GPQGPQ | 0.88 |
| 51 | nicotinoyl-YGYTGA | 0.95 |
| — | — | — |

Example 3

Stability Evaluation of Niacin-Peptides

Figure 2:
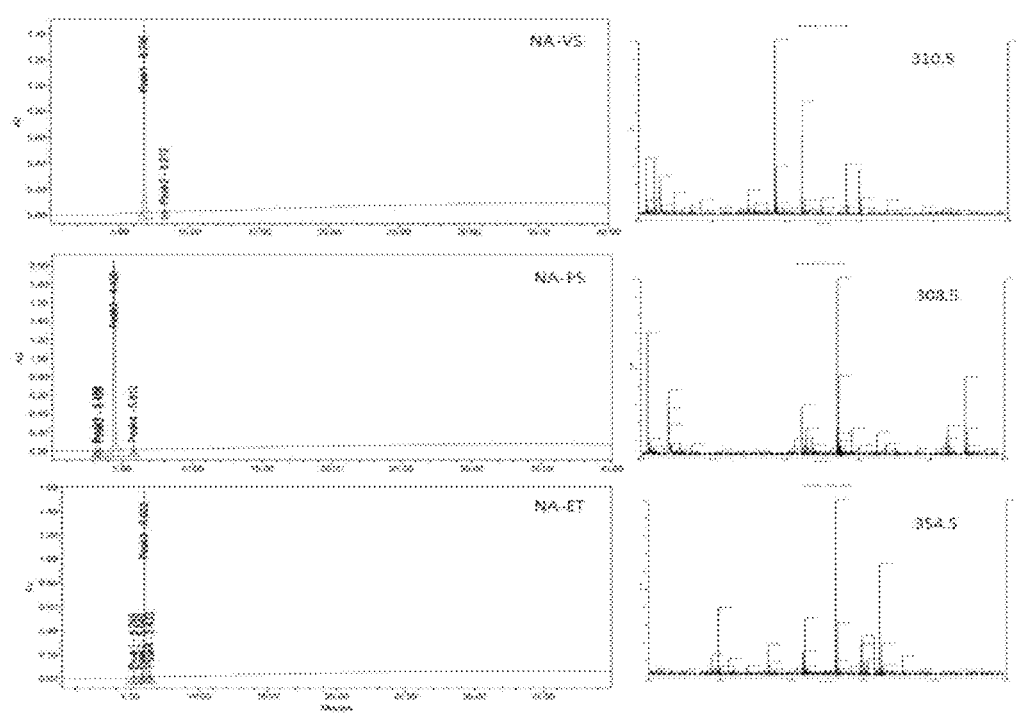
FIG. 2 is graphs showing the results of a high performance liquid chromatography analysis for niacin-peptides.

Following additional mass synthesis of the peptides selected from the libraries, further analyses were carried out using HPLC and MALDI-TOF. FIGS. 2a-2c are HPLC and MALDI-TOF results for NA-VS, NA-PS and NA-ET selected from the library peptides having skin whitening effect.

Figure 3:
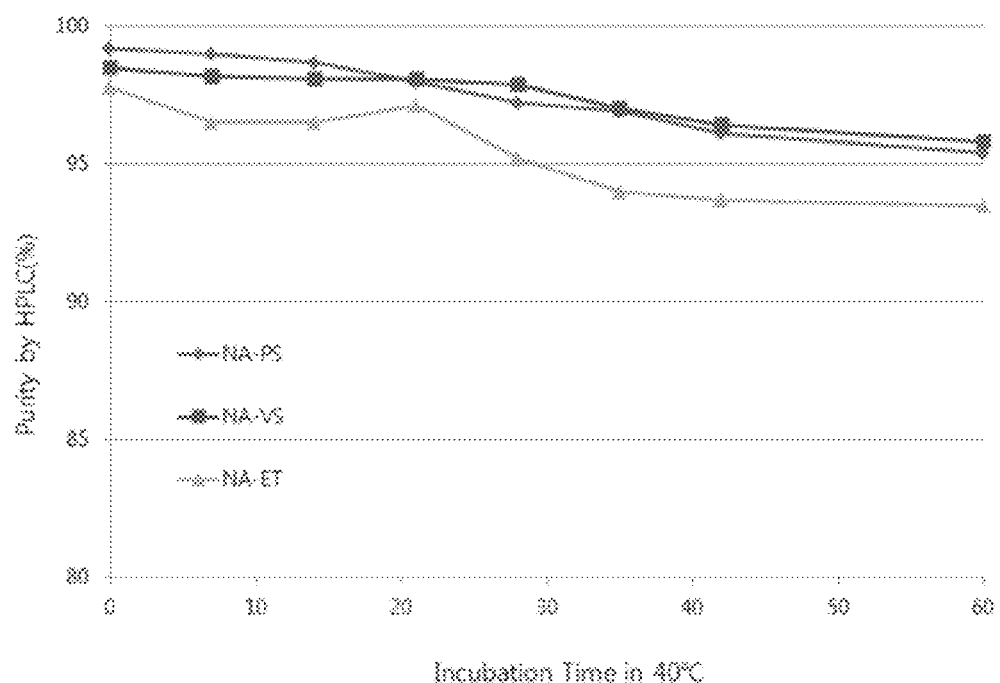
FIG. 3 is a graph showing the measurement results for the heat stability of niacin-peptides.
Figure 4:
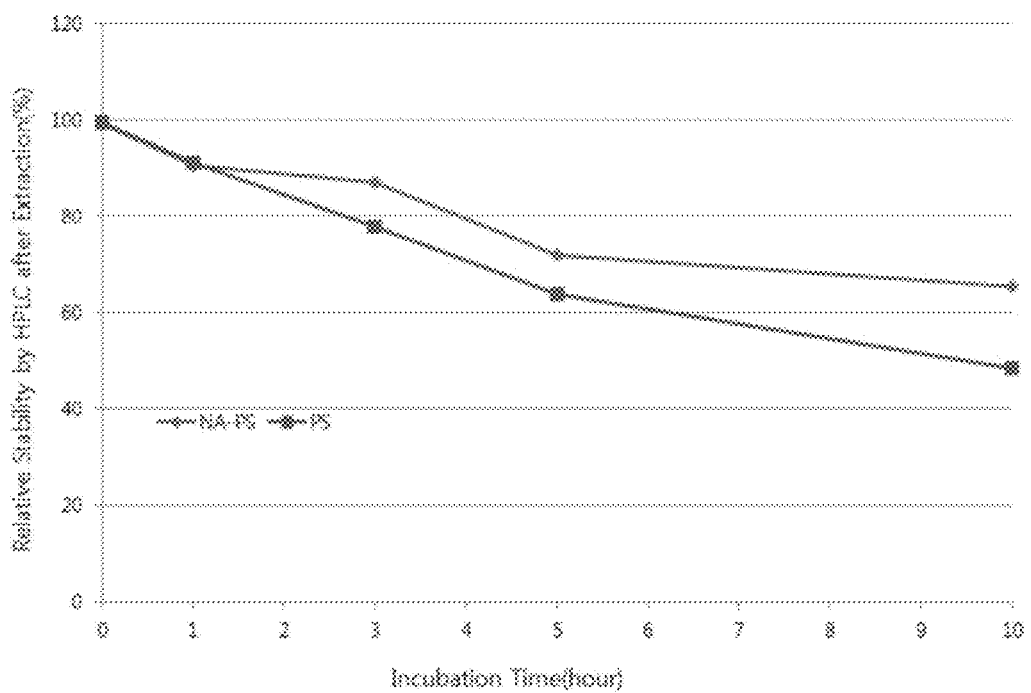
FIG. 4 is a graph showing the results measuring the stability of niacin-peptides in human serum.

To evaluate stability of the prepared peptides, nicotinoyl-VS, nicotinoyl-PS and nicotinoyl-ET peptides with purity of above 98% were dissolved in 50 mM Tris-HCl (pH 8.0) buffer to a concentration of 100 µg/ml. The prepared solutions were introduced into glass vials and kept to stand at 40° C. for 7, 14, 21, 28, 35, 42 and 60 days. The loss of the peptides by heat was analyzed to be no more than 10% until 60 days, demonstrating that the peptides of the present invention have higher heat and storage stability (FIG. 3). The present inventors tested stability of niacin-peptides in human serum. Niacin-peptides (nicotinoyl-PS, 100 µg/ml) or niacin-unlinked peptide (PS, 100 µg/ml) was incubated with human serum for 10 hr, and the amount of residual peptides was measured at every hour. According to the result of the comparative stability experiment, when nicotinoyl-PS (nicotinoyl group linked to the N-terminal of PS peptide) was incubated with the serum for 10 hr, the stability of niacin-peptides was 20% higher than the control group (niacin-unlinked peptide). Thus, it was revealed that niacin-linked peptides are more stable than niacin-unlinked peptides (FIG. 4).

Example 4

Analysis of Skin Whitening Effect of Niacin-Peptides

Cells were treated with various concentrations of niacin-peptide, followed by measuring activity in inhibition of melanogenesis. The mouse melanocytes were cultured at 37° C. in 5% $CO_2$ atmosphere in DMEM supplemented with 10% FBS. The cells were seeded in each well of a 24-well plate ($1 \times 10^5$ cells/well) and their attachment was verified. Cells were incubated with each test group for 3 days: (a) only solvent as negative control; (b) 20 µg/ml α-MSH as a positive control; (c) 20 µg/ml α-MSH plus 1, 10, 100 and 250 µg/ml niacin-peptides (NA-PG, NAPS, NA-ET and NA-VS); (d) 1, 10, 100 and 250 µg/ml arbutin; and (e) 1, 10, 100 and 250 µg/ml AA2G. After centrifugation, the culture medium was removed and the levels of melanogenesis were observed with a naked eye.

Figure 5:
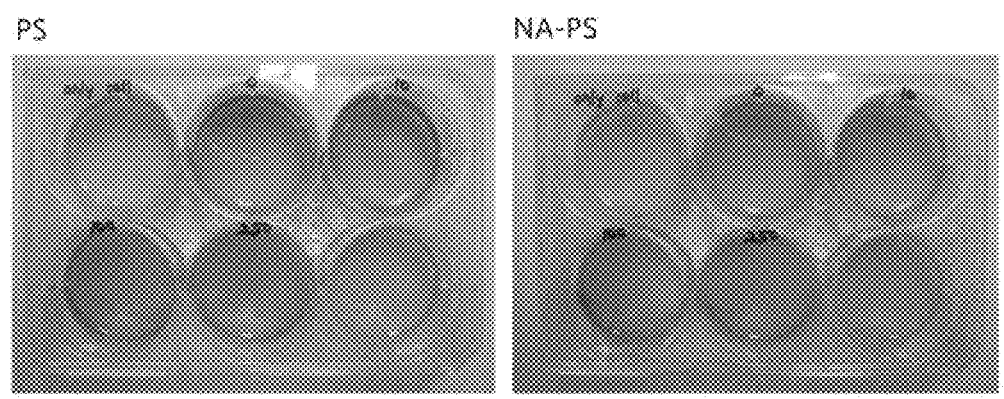
FIG. 5 is photos representing treatment effects of niacin-peptides on melanogenesis decrease in B16F10 cells pretreated with α-MSH.

FIG. 5 is images of melanocytes representing treatment effects of NA-PS and PS peptides on melanogenesis decrease rate in a concentration dependent manner. The cell number was not significantly decreased in the niacin-peptide treated groups compared with that in the α-MSH treated group, while the cell number was significantly decreased in the arbutin treated group. The color of culture medium in the niacin-peptide treated groups became transparent, while little or no change in the cell number was observed, demonstrating the inhibitory effect on melanogenesis occurred.

Figure 6:
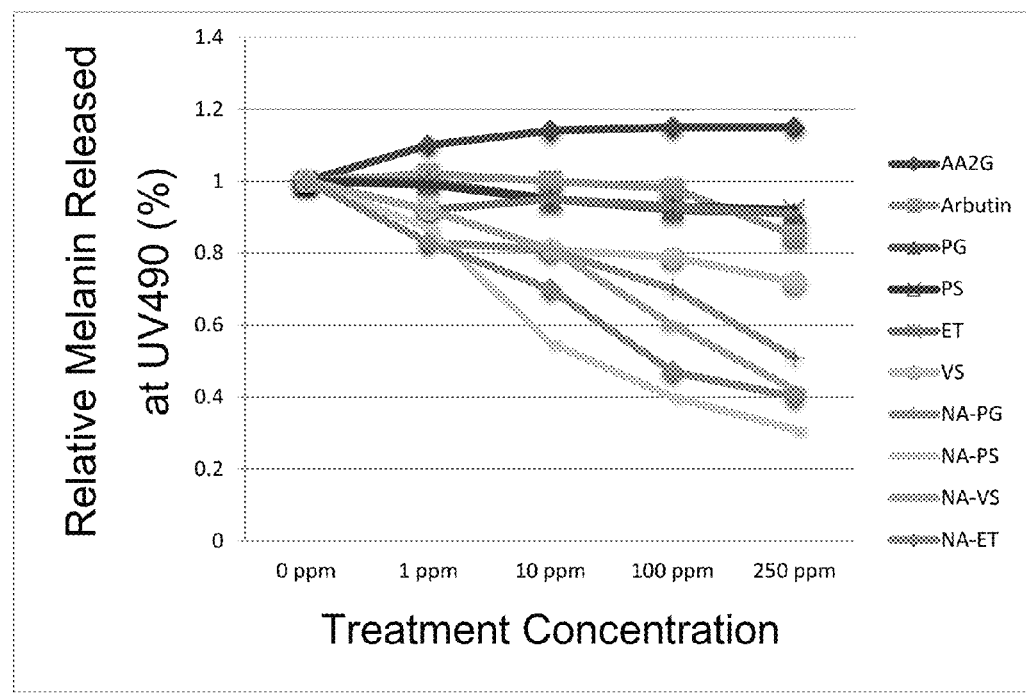
FIG. 6 is a graph showing UV measurement results for treatment effects of niacin-peptides on melanogenesis decrease in B16F10 cells pretreated with α-MSH.

For analyzing the release amount of melanin, the absorbance values of the culture medium were measured at 490 nm. As shown in FIG. 6, the release amount of melanin was apparently decreased in the niacin-peptide treated group compared with that in the control group. These results suggest that the peptide of the present invention may brighten skin tone by inhibition of melanogenesis when melanogenesis-inducing factors act onto skin.

Example 5

Tyrosinase Activity Decrease by Niacin-Peptides

Figure 7:
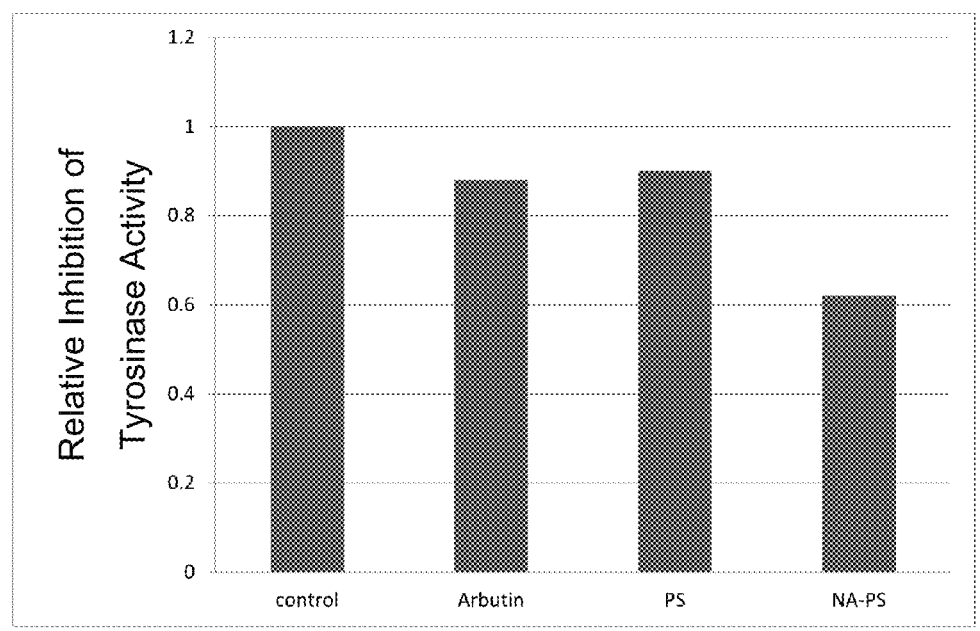
FIG. 7 is a graph showing tyrosinase activity measurement results for treatment effects of niacin-peptides in B16F10 cells pretreated with α-MSH.

Tyrosinase isolated from mushroom was purchased from Sigma. L-Tyrosine was dissolved in phosphate buffer (0.05 M, pH 6.8) to a concentration of 1.5 mM and 0.01 ml of L-tyrosine (1.5 mM) was added to 0.3 ml cuvette, followed by adding 0.01 ml of DOPA (0.06 mM) serving as a cofactor. To the resultant solution, the peptide of the present invention was added and the phosphate buffer was added up to the final volume of 0.1 ml. The solution was incubated with 0.1 ml of tyrosinase solution (60 U/mL) dissolved in phosphate buffer for 10 min at 37° C. The comparative experiments were performed using arbutin, nicotinoyl-PS and PS peptide (100 ppm, respectively). 0.1 ml of phosphate buffer instead of tyrosinase was used as blank. Then, the inhibition rates of tyrosinase were analyzed by measurement of absorbance values at 475 nm on spectrophotometer. Nicotinoyl-PS shows relatively excellent inhibition effects on tyrosinase compared with PS peptide and arbutin (FIG. 7).

Example 6

Inhibition of Expression of Genes Associated with Melanogenesis by Niacin-Peptides To more clearly check activities of niacin-peptides on skin whitening in α-MSH-treated B16F10 melanoma cells, mRNA level of TRP1 (tyrosinase-related protein-1), TRP2 and microphtnalmia-associated transcription factor (MITF) was measured using RT-PCR.

Figure 8:
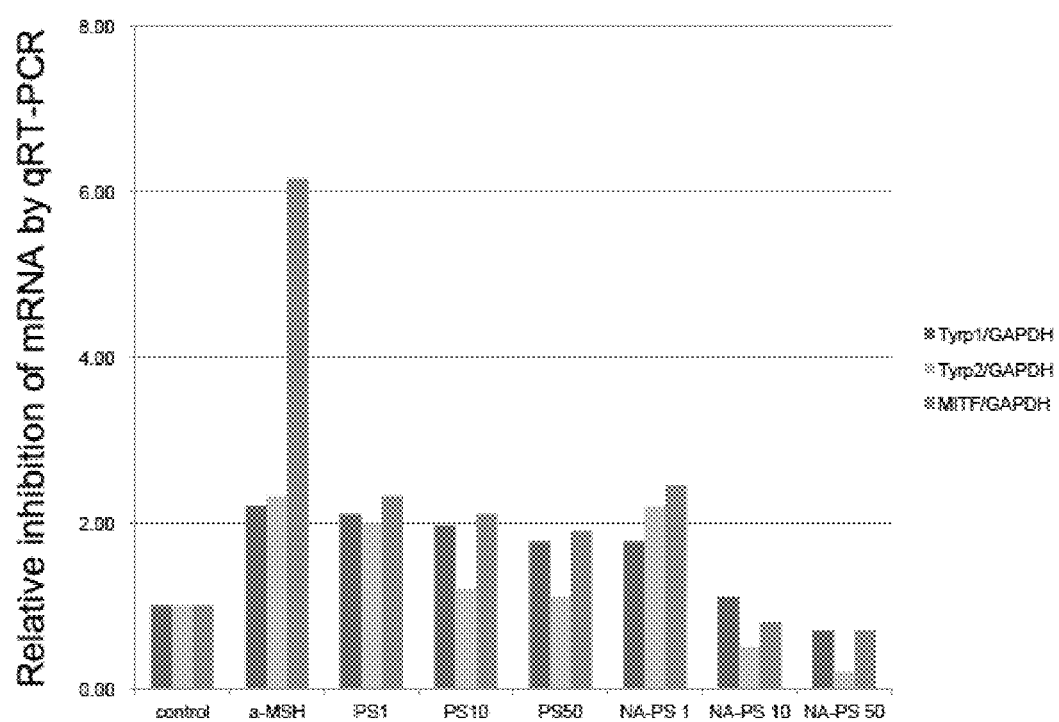
FIG. 8 is photos representing results of reverse transcriptase-polymerase chain reaction analysis using primers for melanogenesis marker genes for treatment effects of niacin-peptides in B16F10 cells pretreated with α-MSH.

First, B16F10 cells were plated at a 6-well plate in a density of 1×10$^5$ cells/well and cultured for 3 days. After cell adhesion was observed, medium was changed with a fresh medium containing 2% serum. Cells were incubated with each test group for 4 days: (a) only solvent as negative control; (b) 20 μg/ml α-MSH as a positive control; (c) 20 μg/ml α-MSH plus 1, 10 and 50 μg/ml peptides (PG, PS, ET and VS); and (d) 20 μg/ml α-MSH plus 1, 10 and 50 μg/ml niacin-peptides (Nicotinoyl-PG, Nicotinoyl-PS, Nicotinoyl-ET and Nicotinoyl-VS). Subsequently, mRNA were extracted from cells and RT-PCR was carried out using primers for TRP1, TRP2 and MITF. The primer sequence is as follows: TRP1 F-primer, 5'-TGGCCCAGGATCAG-TAGGT-3' (SEQ ID NO: 54) and TRP1 R-primer, 5'-CAT-CAACACTTCCAGCA-3' (SEQ ID NO: 55); TRP2 F-primer, 5'-GGCTACAATTACGCCGTTG-3' (SEQ ID NO: 56) and TRP2 R-primer, 5'-CACTGAGAGAGTT-GTGGACCAA-3' (SEQ ID NO: 57); and MITF F-primer, 5'-CTTAACTCCAACTGTGAAAAAGAGG-3' (SEQ ID NO: 58) and MITF R-primer, 5'-CATACCTGGGACT-CACTCTC-3' (SEQ ID NO: 59), GAPDH F-primer, 5'-GAGCCAAACGGGTCATCA-3' (SEQ ID NO: 60) and GAPDH R-primer, 5'-CATATTCGTGGTTCACACC-3' (SEQ ID NO: 61). As a result, it was illustrated that niacin-peptides of the present invention inhibit the expression of TRP-1, TRP-2 and MITF gene associated with melanogenesis in a dose-dependent manner (FIG. 8c).

Example 7

Cytotoxicity Analysis

In order to evaluate peptides of the present invention whether they have cytotoxicity in keratinocytes, MTT assay was carried out using HaCaT kerationcytes (the Korean Cell Line Bank) and NIH3T3 fibroblasts (the Korean Cell Line Bank) according to Rizzino et al. method (Rizzino, et al. Cancer Res., 48: 4266 (1988)). HaCaT ketatinocytes and NIH3T3 fibroblasts were cultured in EMEM (Eagle's minimal essential media; Gibco, USA) supplemented with 10% FBS (fetal bovine serum). Cells cultured were treated with 0.25% trypsin solution to detach cells from the bottom of culture flasks and centrifuged to collect cell pellets. After cells were resuspended in EMEM not containing FBS, its aliquot (1×10$^5$ cells) was added to each well of 96-well plates and cultured under 7% $CO_2$ for 24 hr at 37° C. After 24-hr culture, the medium was changed with a fresh medium without serum and cells were incubated with empty sample (for normalization), nicotinoyl-VS, nicotinoyl-PS, nicotinoyl-ET and nicotinoyl-PG (10 ng/ml, 100 ng/ml, 1 μg/ml, 10 μg/ml and 100 μg/ml, respectively) aseptically dissolved in distilled water and 10% DMSO for 72 hr under the same conditions as described above. After incubation, supernatants were removed and then washed one time using PBS (phosphate buffered saline). After removing PBS, cells were incubated with SRB solution and then sufficiently washed with PBS. Cells were observed under a microscope to find living cell condition. In addition, absorbance at 590 nm was measured to analyze cell viability (FIG. 9).

Figure 9:
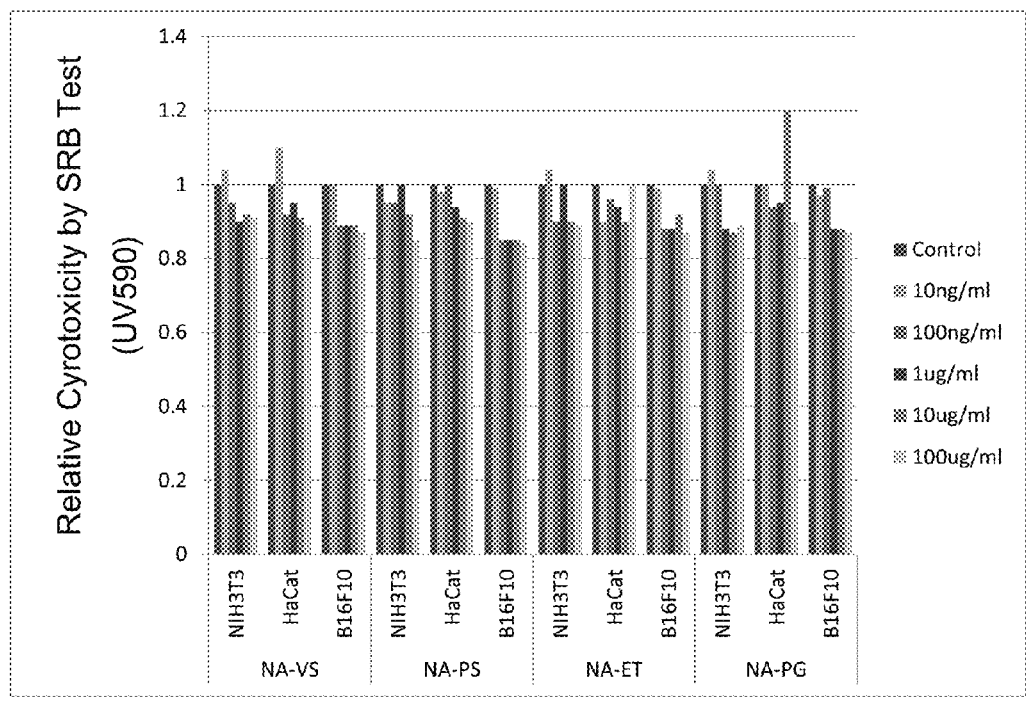
FIG. 9 is a graph showing the cytotoxicity analysis results of niacin-peptides. Niacin-peptides were incubated with HaCat and B16F10 cells and their cytotoxicity was analyzed.

As shown in FIG. 9, the decrease in cell number and changes of cell morphology were not shown in HaCaT and NIH3T3 cells at all concentrations (i.e., low and high concentration) of the peptide under microscope. These results address that the peptide of the present invention induce little or no adverse effects on skin cells.

Example 8

Preparation of Nano Peptides 50 mg of each peptide (nicotinoyl-VS, nicotinoyl-PS, nicotinoyl-ET and nicotinoyl-PG) with skin whitening effect in preparation Examples was dissolved in 500 ml of distilled water by sufficient agitation. The niacin-peptide solution was mixed with 5 g hydrogenated lecithin and a small amount of oils, and its volume was adjusted with distilled water to 1 L. The resulting solution was subjected to a microfluidizer under high pressure for emulsification, thereby providing nanosomes having about 100-nm size. The nanosomes were prepared to have a final concentration of about 50 ppm and used as ingredients for cosmetics.

Example 9

Skin Softener

A skin softener containing one or more of the niacin-peptide nanosomes prepared in Example 2 was formulated according to a commonly employed method as follows:

TABLE 2

| Ingredients | Content (wt %) |
|---|---|
| Niacin-peptide | 0.001 |
| 1,3-butylene glycol | 6.0 |
| Glycerin | 4.0 |
| PEG 1500 | 1.0 |
| Sodium hyaluronate | 1.0 |
| Polysorbate 20 | 0.5 |
| Ethanol | 8.0 |
| Preservative, pigment | Proper amount |
| Benzophenone-9 | 0.05 |
| Perfume | Minute amount |
| Purified water | Residual amount |
| Total | 100 |

Example 10

Nutrient Cream

A nutrient cream containing one or more of the niacin-peptide nanosomes prepared in Example 2 was formulated according to a commonly employed method as follows:

TABLE 3

| Ingredients | Content (wt %) |
| --- | --- |
| Niacin-peptide | 0.001 |
| Meadowfoam oil | 3.0 |
| Cetearylalcohol | 1.5 |
| Stearic acid | 1.5 |
| Glyceryl stearate | 1.5 |
| Liquid paraffin | 10.0 |
| Wax | 2.0 |
| Polysorbate 60 | 0.6 |
| Sorbitan sesquiolate | 2.5 |
| Squalane | 3.0 |
| 1,3-butylene glycol | 3.0 |
| Glycerin | 5.0 |
| Triethanol amine | 0.5 |
| Tocopheryl acetate | 0.5 |
| Preservative, pigments | Proper amount |
| Perfume | Proper amount |
| Purified water | Residual amount |
| Total | 100 |

Example 11

Nutrient Liquid

A nutrient liquid containing one or more of the niacin-peptide nanosomes prepared in Example 2 was formulated according to a commonly employed method as follows:

TABLE 4

| Ingredients | Content (Wt %) |
| --- | --- |
| Niacin-peptide | 0.002 |
| 1,3-butylene glycol | 4.0 |
| Glycerin | 4.0 |
| Cetearyl Alcohol | 0.8 |
| Glyceryl Stearate | 1.0 |
| Triethanol amine | 0.13 |
| Tocopheryl Acetate | 0.3 |
| Liquid paraffin | 5.0 |
| Squalane | 3.0 |
| Makadamianut oil | 2.0 |
| Polysorbate 60 | 1.5 |
| Sorbitan sesquiolate | 0.5 |
| Carboxyvinyl Polymer | 1.0 |
| Preservative, pigments | Proper amount |
| Perfume | Proper amount |
| Purified water | Residual amount |
| Total | 100 |

Example 12

Essence

An essence containing one or more of the niacin-peptide nanosomes prepared in Example 2 was formulated according to a commonly employed method as follows:

TABLE 5

| Ingredients | Content (Wt %) |
| --- | --- |
| Niacin-peptide | 0.005 |
| Glycerin | 10.0 |
| 1,3-butylene glycol | 5.0 |
| PEG 1500 | 2.0 |
| Allantoin | 0.1 |
| DL-panthenol | 0.3 |
| EDTA-2Na | 0.02 |
| Hydroxyethyl cellulose | 0.1 |
| Sodium hyaluronate | 8.0 |
| Carboxyvinyl Polymer | 0.2 |
| Triethanolamine | 0.18 |
| Octyldodeceth-16 | 0.4 |
| Ethanol | 6.0 |
| Perfume, preservative, pigments | Proper amount |
| Purified water | Residual amount |
| Total | 100 |

While the present disclosure has been described with respect to the specific embodiments, it will be apparent to those skilled in the art that various changes and modifications may be made without departing from the spirit and scope of the disclosure as defined in the following claims.

What is claimed is:

1. A peptide having a skin whitening effect, wherein the peptide is selected from the group consisting of nicotinoyl-IF (SEQ ID NO: 1), nicotinoyl-EQ (SEQ ID NO: 2), nicotinoyl-ET (SEQ ID NO: 3), nicotinoyl-FP (SEQ ID NO: 4), nicotinoyl-NI (SEQ ID NO: 5), nicotinoyl-NL (SEQ ID NO: 6), nicotinoyl-NP (SEQ ID NO: 7), nicotinoyl-NY (SEQ ID NO: 8), nicotinoyl-PG (SEQ ID NO: 9), nicotinoyl-PS (SEQ ID NO: 10), nicotinoyl-QI (SEQ ID NO: 11), nicotinoyl-VA (SEQ ID NO: 12), nicotinoyl-VF (SEQ ID NO: 13), nicotinoyl-VS (SEQ ID NO: 14), nicotinoyl-VT (SEQ ID NO: 15), nicotinoyl-WM (SEQ ID NO: 16), nicotinoyl-YR (SEQ ID NO: 17), nicotinoyl-YT (SEQ ID NO: 18), nicotinoyl-AHK (SEQ ID NO: 19), nicotinoyl-FWY (SEQ ID NO: 20), nicotinoyl-GHR (SEQ ID NO: 21), nicotinoyl-GPHyp (SEQ ID NO: 22), nicotinoyl-KVK (SEQ ID NO: 23), nicotinoyl-TYR (SEQ ID NO: 24), nicotinoyl-YGY (SEQ ID NO: 25), nicotinoyl-PLG-NH2 (SEQ ID NO: 26), nicotinoyl-beta-AHSH (SEQ ID NO: 27), nicotinoyl-DKYV (SEQ ID NO: 28), nicotinoyl-GEPG (SEQ ID NO: 29), nicotinoyl-GQPR (SEQ ID NO: 30), nicotinoyl-GRKG (SEQ ID NO: 31), nicotinoyl-KAKA (SEQ ID NO: 32), nicotinoyl-SSNA (SEQ ID NO: 33), nicotinoyl-VPAA (SEQ ID NO: 34), nicotinoyl-YPFF-NH2 (SEQ ID NO: 35), nicotinoyl-GPRPA-NH2 (SEQ ID NO: 36), nicotinoyl-ISELGW (SEQ ID NO: 37), nicotinoyl-KLAKK (SEQ ID NO: 38), nicotinoyl-KRGDR (SEQ ID NO: 39), nicotinoyl-KRGKP (SEQ ID NO: 40), nicotinoyl-KTTKS (SEQ ID NO: 41), nicotinoyl-KVARP (SEQ ID NO: 42), nicotinoyl-RKDVY (SEQ ID NO: 43), nicotinoyl-YGGFL (SEQ ID NO: 44), nicotinoyl-YGGFM (SEQ ID NO: 45), nicotinoyl-SIKVAV (SEQ ID NO: 46), nicotinoyl-VEPIPY (SEQ ID NO: 47), nicotinoyl-VGVAPG (SEQ ID NO: 48), nicotinoyl-EEMQRR-NH2 (SEQ ID NO: 49), nicotinoyl-GPQGPQ (SEQ ID NO: 50) and nicotinoyl-YGYTGA (SEQ ID NO: 51).

2. The peptide according to claim 1, wherein the peptide inhibits melanogenesis.

3. The peptide according to claim 1, wherein the peptide inhibits the activity of tyrosinase.

4. The peptide according to claim 1, wherein the peptide inhibits the expression of tyrosinase-related protein-1 (Trp-1).

5. The peptide according to claim 1, wherein the peptide inhibits the expression of tyrosinase-related protein-2 (Trp-2).

6. The peptide according to claim 1, wherein the peptide inhibits the expression of microphtnalmia-associated transcription factor (MITF).

7. A composition for skin whitening, wherein the composition comprising a peptide selected from the group consisting of nicotinoyl-IF (SEQ ID NO: 1), nicotinoyl-EQ (SEQ ID NO: 2), nicotinoyl-ET (SEQ ID NO: 3), nicotinoyl-FP (SEQ ID NO: 4), nicotinoyl-NI (SEQ ID NO: 5), nicotinoyl-NL (SEQ ID NO: 6), nicotinoyl-NP (SEQ ID NO: 7), nicotinoyl-NY (SEQ ID NO: 8), nicotinoyl-PG (SEQ ID NO: 9), nicotinoyl-PS (SEQ ID NO: 10), nicotinoyl-QI (SEQ ID NO: 11), nicotinoyl-VA (SEQ ID NO: 12), nicotinoyl-VF (SEQ ID NO: 13), nicotinoyl-VS (SEQ ID NO: 14), nicotinoyl-VT (SEQ ID NO: 15), nicotinoyl-WM (SEQ ID NO: 16), nicotinoyl-YR (SEQ ID NO: 17), nicotinoyl-YT (SEQ ID NO: 18), nicotinoyl-AHK (SEQ ID NO: 19), nicotinoyl-FWY (SEQ ID NO: 20), nicotinoyl-GHR (SEQ ID NO: 21), nicotinoyl-GPHyp (SEQ ID NO: 22), nicotinoyl-KVK (SEQ ID NO: 23), nicotinoyl-TYR (SEQ ID NO: 24), nicotinoyl-YGY (SEQ ID NO: 25), nicotinoyl-PLG-NH2 (SEQ ID NO: 26), nicotinoyl-beta-AHSH (SEQ ID NO: 27), nicotinoyl-DKYV (SEQ ID NO: 28), nicotinoyl-GEPG (SEQ ID NO: 29), nicotinoyl-GQPR (SEQ ID NO: 30), nicotinoyl-GRKG (SEQ ID NO: 31), nicotinoyl-KAKA (SEQ ID NO: 32), nicotinoyl-SSNA (SEQ ID NO: 33), nicotinoyl-VPAA (SEQ ID NO: 34), nicotinoyl-YPFF-NH2 (SEQ ID NO: 35), nicotinoyl-GPRPA-NH2 (SEQ ID NO: 36), nicotinoyl-ISELGW (SEQ ID NO: 37), nicotinoyl-KLAKK (SEQ ID NO: 38), nicotinoyl-KRGDR (SEQ ID NO: 39), nicotinoyl-KRGKP (SEQ ID NO: 40), nicotinoyl-KTTKS (SEQ ID NO: 41), nicotinoyl-KVARP (SEQ ID NO: 42), nicotinoyl-RKDVY (SEQ ID NO: 43), nicotinoyl-YGGFL (SEQ ID NO: 44), nicotinoyl-YGGFM (SEQ ID NO: 45), nicotinoyl-SIKVAV (SEQ ID NO: 46), nicotinoyl-VEPIPY (SEQ ID NO: 47), nicotinoyl-VGVAPG (SEQ ID NO: 48), nicotinoyl-EEMQRR-NH2 (SEQ ID NO: 49), nicotinoyl-GPQGPQ (SEQ ID NO: 50) and nicotinoyl-YGYTGA (SEQ ID NO: 51).

8. The composition according to claim 7, where the composition is a cosmetic composition.

* * * * *